US006623457B1

(12) United States Patent
Rosenberg

(10) Patent No.: US 6,623,457 B1
(45) Date of Patent: Sep. 23, 2003

(54) METHOD AND APPARATUS FOR THE TRANSDERMAL ADMINISTRATION OF A SUBSTANCE

(75) Inventor: Zeil B. Rosenberg, Closter, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/401,452

(22) Filed: Sep. 22, 1999

(51) Int. Cl.[7] ............................................... A61M 5/00
(52) U.S. Cl. ...................................... 604/191; 604/272
(58) Field of Search .............................. 604/258, 890.1, 604/85, 183, 184, 239, 261, 180, 263, 192, 191, 272, 80, 173; 424/449, 483

(56) References Cited

U.S. PATENT DOCUMENTS

| | | |
|---|---|---|
| 3,595,231 A | 7/1971 | Pistor |
| 3,814,097 A | 6/1974 | Ganderton et al. |
| 3,964,482 A | 6/1976 | Gerstel et al. |
| 5,250,023 A | 10/1993 | Lee et al. |
| 5,879,326 A | 3/1999 | Godshall et al. |
| 5,968,021 A * | 10/1999 | Ejlersen .................. 604/263 |
| 6,219,574 B1 * | 4/2001 | Cormier et al. ............. 604/20 |
| 6,256,533 B1 * | 7/2001 | Yuzhakov et al. ........... 604/20 |

FOREIGN PATENT DOCUMENTS

| | | |
|---|---|---|
| CA | 2241615 | 6/1998 |
| EP | 0497620 A2 | 1/1992 |
| WO | WWO 97/48440 | 12/1997 |
| WO | WO 98/00193 | 1/1998 |

* cited by examiner

Primary Examiner—Michael J. Hayes
Assistant Examiner—Mark K. Han
(74) Attorney, Agent, or Firm—Venable LLP; Richard D. Schmidt; Eric M. Lee

(57) ABSTRACT

A transdermal delivery device includes a plurality of microneedles for injecting a substance such as a pharmaceutical agent into or below the stratum corneum of the skin. The device has housing formed from a top and bottom wall to define a chamber for containing a pharmaceutical agent. An inlet port is provided in the top wall of the housing for supplying the pharmaceutical agent to the chamber and directing the agent to the microneedles. The housing can have a Luer lock type fitting for coupling with a syringe having a Luer lock collar to inject the pharmaceutical agent into the housing. The housing can be divided into a plurality of chambers by an internal wall for supplying different agents simultaneously or sequentially to a patient. The microneedles have a length of about 5–250 microns and generally about 50–100 microns.

13 Claims, 8 Drawing Sheets

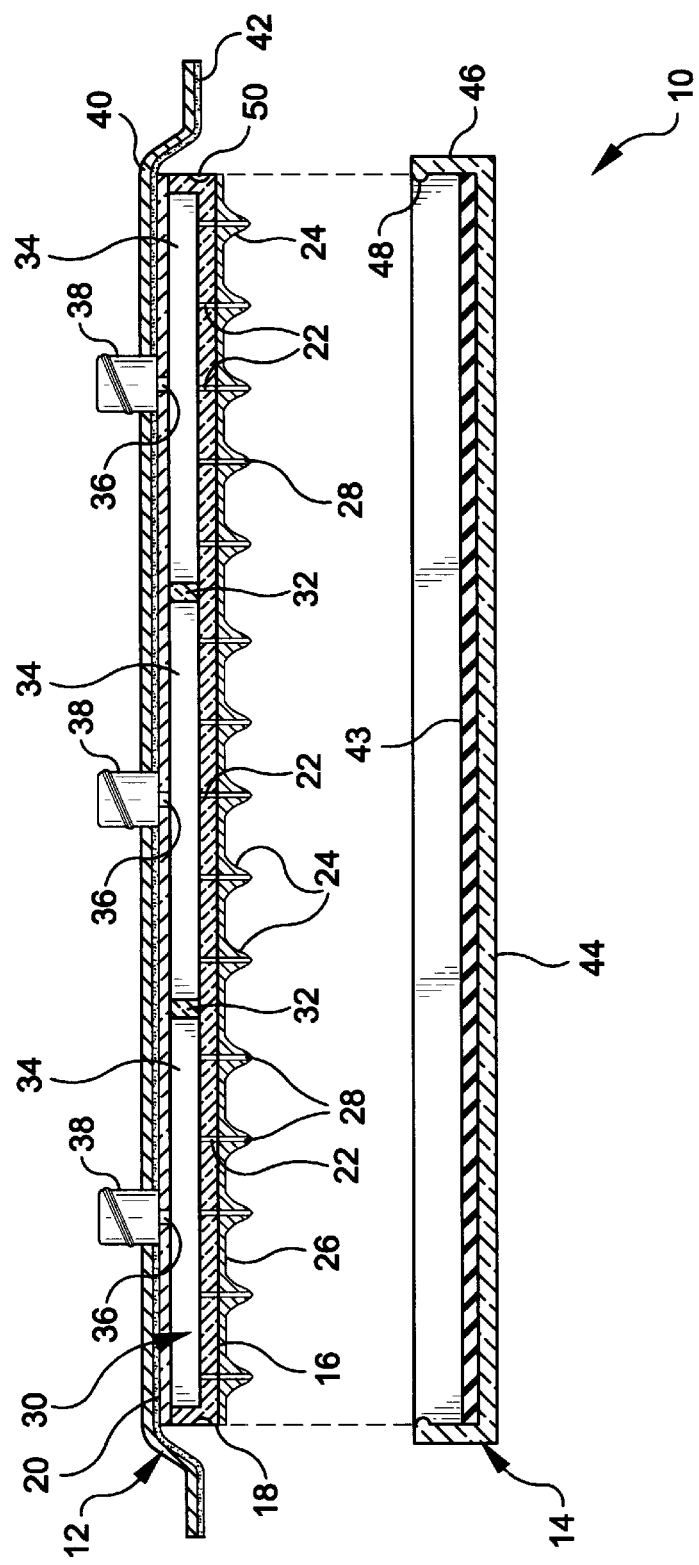

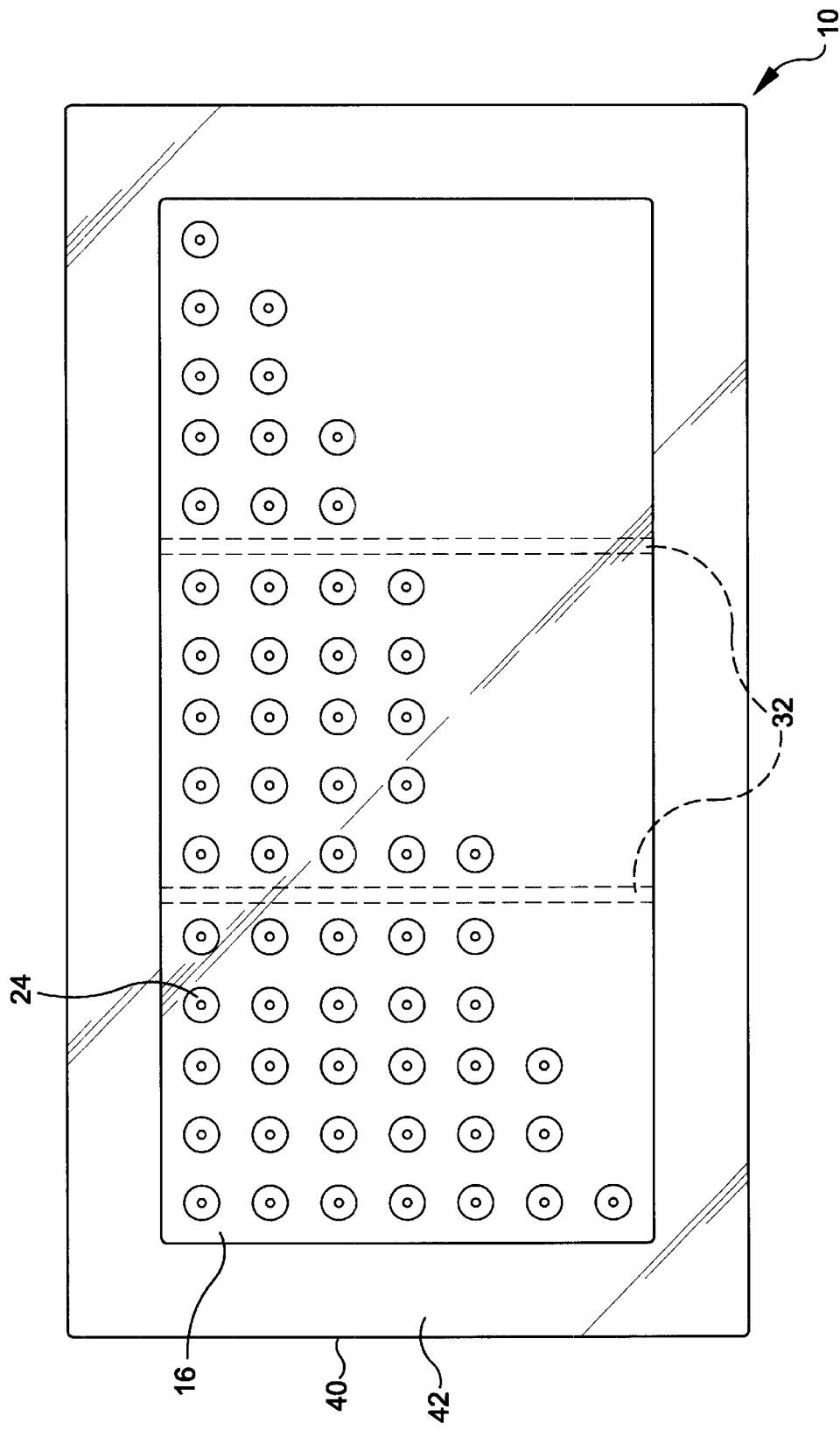

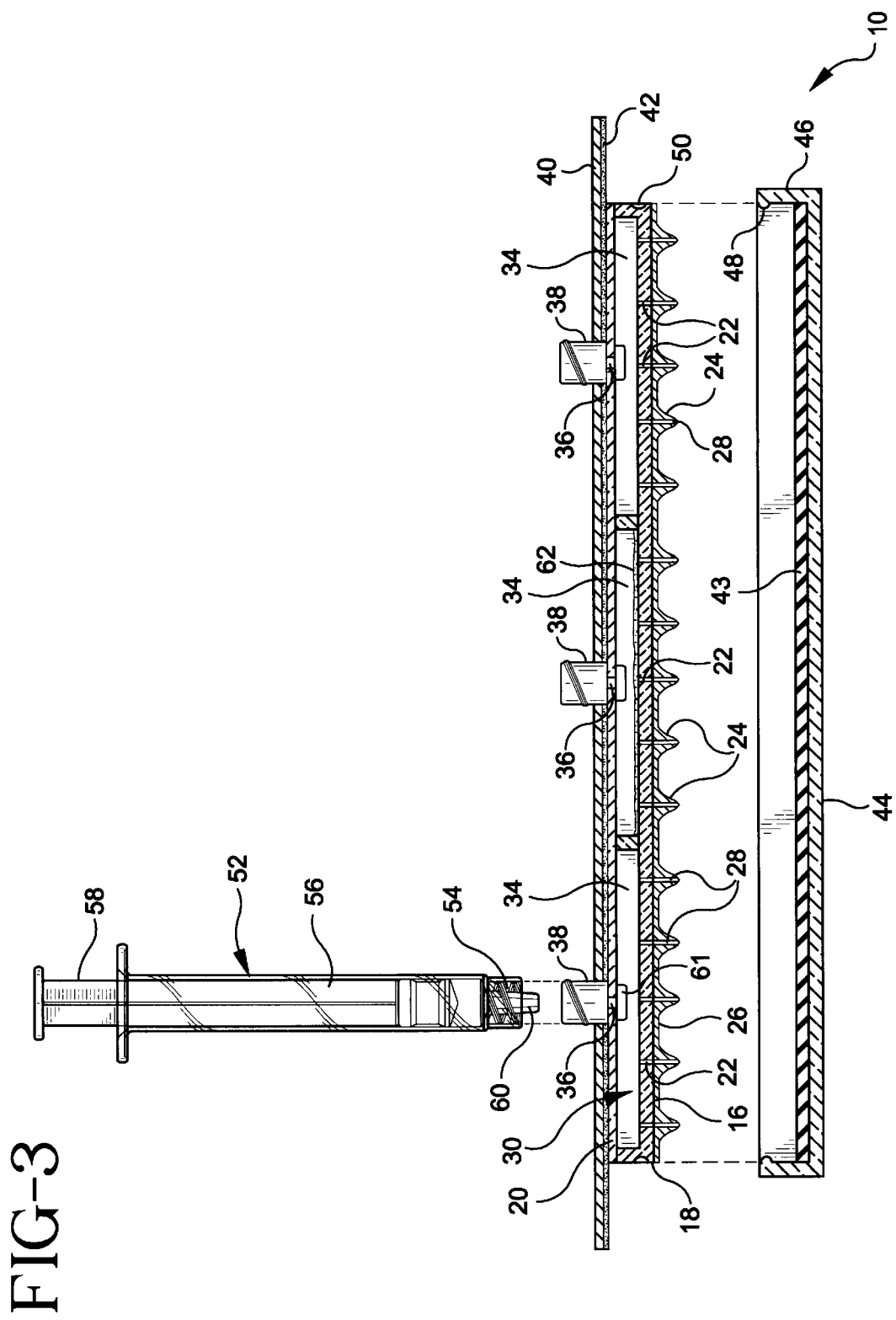

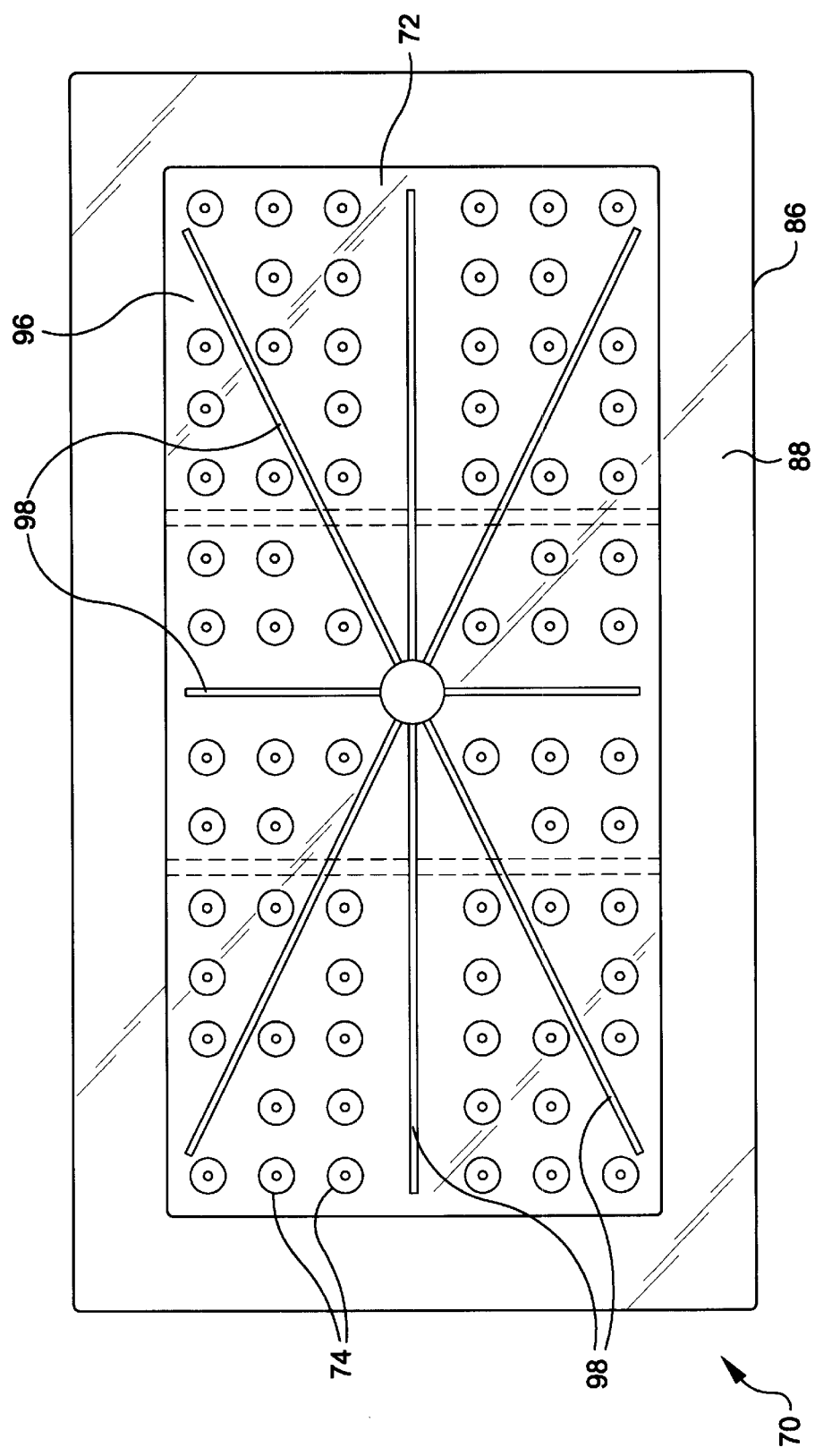

METHOD AND APPARATUS FOR THE TRANSDERMAL ADMINISTRATION OF A SUBSTANCE

FIELD OF THE INVENTION

The present invention relates to a method and apparatus for delivering a substance and particularly a pharmaceutical agent transdermally to a patient. More particularly, the invention is directed to a method and apparatus for delivering a pharmaceutical agent such as a vaccine to a patient through the stratum corneum.

BACKGROUND OF THE INVENTION

The skin is made up of several layers with the upper composite layer being the epithelial layer. The outermost layer of the skin is the stratum corneum which has well known barrier properties to prevent molecules and various substances from entering the body and analytes from exiting the body. The stratum corneum is a complex structure of compacted keratinized cell remnants having a thickness of about 10–30 microns. The stratum corneum forms a waterproof membrane to protect the body from invasion by various substances and the outward migration of various compounds.

The natural impermeability of the stratum corneum prevents the administration of most pharmaceutical agents and other substances through the skin. Numerous methods and devices have been proposed to enhance the permeability of the skin and to increase the diffusion of various drugs through the skin so that the drugs can be utilized by the body. Typically, the delivery of drugs through the skin is enhanced by either increasing the permeability of the skin or increasing the force or energy used to direct the drug through the skin.

One example of a method for increasing the delivery of drugs through the skin include iontophoresis. Iontophoresis generally applies an external electrical field to ionize the drug, thereby increasing the diffusion of the drug through the skin. Iontophoresis can be difficult to control the amount and rate of drug delivery. Under some circumstances, iontophoresis can cause skin damage depending on the extent of ionization, the energy applied to ionize the drug and duration of the treatment.

Sonic, and particularly ultrasonic energy, has also been used to increase the diffusion of drugs through the skin. The sonic energy is typically generated by passing an electrical current through a piezoelectric crystal or other suitable electromechanical device. Although numerous efforts to enhance drug delivery using sonic energy have been proposed, the results generally show a low rate of drug delivery.

Another method of delivering drugs through the skin is by forming micropores or cuts through the stratum corneum. By penetrating the stratum corneum and delivering the drug to the skin in or below the stratum corneum, many drugs can be effectively administered. The devices for penetrating the stratum corneum generally include a plurality of micron size needles or blades having a length to penetrate the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

Transdermal drug delivery is also known to use pulsed laser light to ablate the stratum corneum without significant ablation or damage to the underlying epidermis. A drug is then applied to the ablated area and allowed to diffuse through the epidermis.

The prior methods and apparatus for the transdermal administration of drugs has exhibited limited success. Accordingly, a continuing need exists in the industry for an improved device for the administration of various drugs and other substances.

SUMMARY OF THE INVENTION

The present invention is directed to a method and apparatus for the transdermal delivery of a substance, such as a drug, vaccine or other pharmaceutical agent, to a patient. In particular, the invention is directed to a method and apparatus for delivering a pharmaceutical agent to the stratum corneum of the skin to a sufficient depth where the pharmaceutical agent can be absorbed and utilized by the body. In embodiments where the pharmaceutical agent is a vaccine, the vaccine is introduced into the intradermal tissue below the stratum corneum where the vaccine can generate an immune response.

Accordingly, a primary object of the invention is to provide a method and apparatus for efficiently administering a pharmaceutical agent transdermally through the skin substantially without pain to the patient.

Another object of the invention is to provide an apparatus having a plurality of microneedles or blades for penetrating the stratum corneum of the skin for delivering a pharmaceutical agent or other substance to the skin.

A further object of the invention is to provide an apparatus for delivering a plurality of drugs transdermally to an animal either simultaneously or sequentially.

Another object of the invention is to provide a method for transdermally delivering one or more vaccines simultaneously or sequentially in small doses.

A further object of the invention is to provide a method and apparatus for the transdermal delivery of multiple vaccines without the need for vaccine reformulation or combination.

A still further object of the invention is to provide an apparatus for the transdermal delivery of a pharmaceutical agent having a plurality of microneedles for penetrating the stratum corneum and a coupling member for coupling with a supply container for supplying a pharmaceutical agent to the microneedles.

Another object of the invention is to provide an apparatus having a plurality of microneedles for penetrating the stratum corneum and an outer adhesive patch for adhesively attaching the apparatus to the skin of a patient.

Still another object of the invention is to provide a transdermal pharmaceutical delivery device having an array of microneedles for penetrating the stratum corneum of the skin, where the device has a channel in a bottom surface for directing a fluid containing a pharmaceutical agent from a source to the microneedles.

A further object of the invention is to provide a device for the transdermal delivery of a substance to a patient where the device has an array of microneedles and a dried substance, the dried substance being reconstituted by introducing a solvent or carrier through the device and then delivered to a patient.

These and other objects of the invention are substantially attained by providing an intradermal delivery device for introducing a substance into the skin of a patient. The device comprises a top wall having a top surface, a bottom surface, and at least one opening extending between the top and bottom surfaces. A bottom wall is coupled to the top wall and spaced therefrom to define a reservoir therebetween for containing the substance. The bottom wall has an inner surface and an outer surface which have a plurality of openings. A coupling member is attached to the top surface of the top wall for supplying the substance through the openings in the top wall and into the reservoir. A plurality of microneedles are coupled to the outer surface of the bottom wall and are in communication with the openings in the bottom wall for directing the substance from the reservoir to the skin of a patient. The microneedles have a length sufficient to penetrate the stratum corneum of the skin without piercing or passing completely through the epidermis. The actual length of the microneedles can vary to optimize the delivery for the particular substance being administered. For example, the microneedles for administering a vaccine can have a length to pass through the stratum corneum into the other skin layers where deposition of vaccine and/or adjuvant can generate a desired immune response. This would normally follow interaction or uptake with various mechanisms that produce such responses, for example, uptake and antigen processing by Langerhans cells.

The objects and advantages of the invention are further attained by providing an intradermal device for administering a pharmaceutical agent through the skin of a patient. The device comprises a substantially planar base having a top surface, a bottom surface and an opening extending between the top and bottom surfaces. A coupling member is attached to the top surface of the base for directing a fluid containing a pharmaceutical agent through the opening in the base and for coupling to a fluid source. A plurality of microneedles are attached to and extend from the bottom surface of the base and have a length sufficient to penetrate the stratum corneum of the skin. A plurality of channels are formed in the bottom surface of the base and extend from the opening outwardly toward an outer edge of the base. The channels are positioned between the microneedles for directing a fluid from the opening to the microneedles.

The objects of the invention are further attained by providing an intradermal delivery device for delivering a substance, such as a pharmaceutical agent, to a patient. The device comprises a syringe having a syringe barrel with an outlet tip and a plunger for dispensing a liquid in the syringe. A plurality of microneedles are coupled to the tip. The microneedles can have a length sufficient to penetrate the stratum corneum of the skin and have channels which extend through the microneedles for delivering the pharmaceutical agent to a patient.

Another object of the invention is to provide a method of administering a pharmaceutical agent through the skin of a patient which comprises providing an intradermal device having a body with a top surface, a bottom surface, and at least one opening extending between the top and bottom surfaces. A plurality of microneedles are attached to and extend from the bottom surface of the body and can have a length sufficient to penetrate the stratum corneum of the skin. The device contacts the skin of a patient and sufficient pressure is applied for the microneedles to penetrate the stratum corneum of the patient. A pharmaceutical agent or other substance is delivered to the microneedles so that the substance is absorbed through the skin.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which:

FIG. 1 is a side elevational view in cross-section of a transdermal delivery device in accordance with a first embodiment of the invention;

FIG. 2 is a bottom view of the transdermal delivery device of FIG. 1 with the cover removed;

FIG. 3 is a side view of the transdermal delivery device of FIG. 1 showing a syringe for supplying the device with a pharmaceutical agent;

FIG. 7 is a bottom view of the transdermal delivery device of FIG. 4, showing the channels for directing the pharmaceutical agent from the supply container to the microneedles;

DETAILED DESCRIPTION OF THE PREFERRED EMBODIMENTS

Figure 3A:
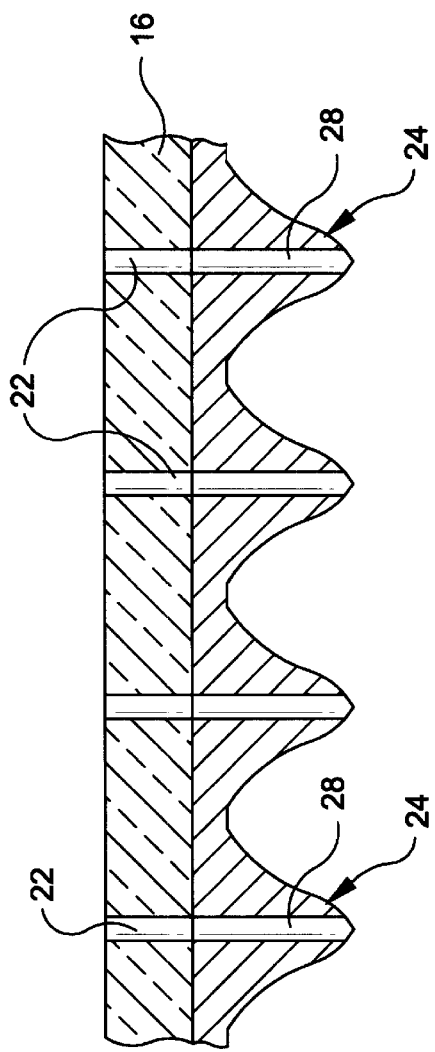
FIG. 3A is a partial side view in cross-section of the microneedles.

The present invention is directed to an intraepidermal delivery device for administering a substance to a patient. More particularly, the invention is directed to a delivery device and to a method for administering a substance into or below the stratum corneum of the skin of a patient. As used herein, the term penetrate refers to entering a layer of the skin without necessarily passing completely through. Piercing refers to passing completely through a layer of the skin. As used herein, transdermal refers to the delivery of a substance, such as a pharmaceutical, biological agent or vaccine, through one or more layers of skin. Intradermal refers to one or more layers within the skin and not limited to the dermis layer of the skin.

The device and method of the present invention are particularly suitable for use in administering various substances, including pharmaceutical agents, to a patient, and particularly to a human patient. As used herein, a pharmaceutical agent includes a substance having biological activity that can be delivered through the body membranes and surfaces, and particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, adjuvants, biologics, and the like. Other substances which can be delivered intradermally to a patient include proteins, peptides and fragments thereof. The proteins and peptides can be naturally occurring, synthesized or recombinantly produced.

In some embodiments of the present invention, a vaccine is administered using the device and method of the invention. The multipuncture device of the invention is believed in addition to have a unique immunological advantage in the delivery of vaccines with the potential of increasing the vaccine's clinical value. The insertion of the multiple needle points into the tissue is suggested as having an adjuvant-like stimulatory effect. The needle stick response from multiple microneedle points is believed more than a simple acute inflammatory response. Needle sticks can cause damage to a variety of cells and cellular architecture, causing the appearance of polymorphonuclear neutrophil (PMN) and microphages as well as the release of cytokines, including ILI, tumor necrosis factor (TNF) and other agents, which can lead to a number of other immunological responses. The soluble stimulatory factors influence the proliferation of lymphocytes and are central to the immune response to vaccines. The immune stimulation is proportional to the direct needle-cell interaction.

The microneedle device of the present invention is valuable in promoting significant immune response to a vaccine by delivering a vaccine below the stratum corneum and into the cells of the tissue. The microneedles can have a length to penetrate and pass through the stratum corneum without penetrating the dermis to minimize absorption of the vaccine into the bloodstream. The small intracellular depots created by the microneedle array are believed to increase the availability of the vaccine antigen for interaction with antigen presenting cells more than would a vaccine deposited by standard needles in a larger depot quantity. In further embodiments, the microneedles can have a length to penetrate, but not pierce, the stratum corneum.

The microneedle array of the invention is believed to magnify several-fold the trivial or inconsequential immune stimulatory impact of a single needlestick independent of the route of delivery and vaccine. The microneedle delivery device facilitates and enhances vaccine immunogenicity by an adjuvant-like immune stimulation.

The primary barrier properties of the skin including the resistance to drug penetration reside in the outermost layer of the skin, referred to as the stratum corneum. The inner layers of the epidermis generally include three layers, commonly identified as the stratum granulosum, the stratum malpighii, and the stratum germinativum. Once a drug or other substance penetrates below the stratum corneum, there is substantially less resistance to permeation into the subsequent layers of the skin and eventual absorption by the body. Thus, delivery of a substance below the stratum corneum can be an effective system for administering some substances, and particularly some vaccines, to the body. The present invention is primarily directed to a device and method for delivering a substance, and particularly a pharmaceutical agent, into or below the stratum corneum for administering the substance or pharmaceutical agent to the patient. Preferably, the device and method of the invention pierce the stratum corneum substantially without penetrating the dermis to target the tissue layers below the stratum corneum. It is of potential benefit for vaccines to target presentation of antigen to various antigen presenting cells and other immunostimulatory sites, such as Langerhans cells and intraepithelial cells, as well as proximal delivery of adjuvants.

Referring to FIG. 1, the device 10 includes a body portion 12 and a cover 14. The body 12 includes a bottom wall 16, side walls 18 and a top wall 20 to form a reservoir 30. The bottom wall 16 includes a plurality of spaced apart openings 22 extending completely through the bottom wall 16. The openings 22 are arranged in an array of rows and columns. The openings are generally uniformly spaced apart, although the spacing can be non-uniform or it can alternate between small and large.

In the embodiment of FIGS. 1–3A, a plurality of hollow microneedles 24 are provided on the bottom surface 26 of the bottom wall 16 to form an array. Each of the microneedles 24 include a passage or opening 28 passing through the length of the microneedle 24 and communicating with the opening 22 in the bottom wall 16. The openings 22 and 28 define a continuous channel to communicate with the reservoir 30 to access the fluid in the reservoir 30. The openings 22 and 28 have a diameter sufficient to allow a fluid to pass from the reservoir to the microneedle tips at a suitable rate to deliver the substance to the skin. The dimensions of the openings 22 and 28 will depend on the substance being administered and the rate of absorption for the substance by the tissue.

In the embodiment shown in FIGS. 3 and 3A, microneedles 24 are formed from a substrate such as a silicon wafer or plastic substrate. The microneedles are attached to the bottom wall 16 of the body 12. In further embodiments, the microneedles can be integrally formed with the bottom wall so that the substrate of the microneedles can form the bottom wall of the body.

As shown in FIG. 3, the side walls 18 in the embodiment illustrated extend substantially perpendicular to the bottom wall 16 and are coupled to the top wall 20 to define the reservoir 30. In the embodiment illustrated, intermediate walls 32 extend between the bottom wall 16 and the top wall 20 to divide the reservoir 30 into three separate chambers 34. Preferably, the intermediate walls 32 prevent fluid communication between the adjacent chambers 34.

The top wall 20 includes several openings 36, with each opening 36 defining a passageway into one of the chambers 34. A coupling member 38 is attached to the top wall 20 surrounding each of the openings 36. In the embodiment illustrated, the coupling members 38 are externally threaded Luer lock type fittings as known in the art. Alternatively, other coupling members can be used, such as rubber, septum or one-way valve.

A flexible cover sheet 40 having an adhesive layer 42 is attached to the top wall 20 to form an adhesive patch for attaching the device to the skin of a patient. As shown in FIGS. 1 and 2, the cover sheet 40 has a dimension greater than the dimension of the body portion 12 so that the cover sheet 40 has an overhanging edge portion 41 extending beyond the edges of the body 12 with an exposed area of adhesive. The cover sheet 40 has a length and width greater than the body portion 12 to enable the adhesive layer 42 of the overhanging portion 41 to completely surround the body portion 12 and adhere to the skin of the patient and thereby attach the delivery device to the patient. The adhesive 42 is generally a pressure sensitive adhesive which will not irritate the skin and can be easily removed from the skin without injury. A release sheet can be attached to the overhanging edge portion 41 which can be peeled away to expose the adhesive prior to use. In further embodiments, the cover sheet overhangs the body portion 12 at opposite ends.

The removable cover 14 in the embodiment of FIGS. 1 and 3 has an outer wall 44 and a side wall 46. Side wall 46 includes a detent 48 which is received in a recess 50 in the side wall 18 of the body portion 12. The cover 14 snaps onto the body portion to protect the microneedles 24 and can be removed prior to use. A resilient pad 43 is optionally provided on the inner surface of the outer wall 44 to contact the tips of the microneedles 24 to seal the openings in the microneedles 24 without damaging the microneedles.

The delivery device 10 is generally made from a plastic material that is non-reactive with the substance being administered. Suitable plastic materials include, for example, polyethylene, polypropylene, polyesters, polyamides and polycarbonates as known in the art. The microneedles can be made from various materials as known in the art. For example, microneedles can be made from silicon, stainless steel, tungsten steel, alloys of nickel, molybdenum, chromium, cobalt, and titanium, ceramics, glass polymers and other non-reactive metals, and alloys thereof.

The length and thickness of the microneedles are selected based on the particular substance being administered and the thickness of the stratum corneum in the location where the device is to be applied. Preferably, the microneedles penetrate the stratum corneum substantially without penetrating or passing through the epidermis. The microneedles can have a length for penetrating the skin up to about 250 microns. Suitable microneedles have a length of about 5 to 200 microns. Typically, the microneedles have a length of about 5 to about 100 microns, and generally in the range of about 50 to 100 microns. The microneedles in the illustrated embodiment have a generally conical shape. In alternative embodiments, the microneedles can be triangles, flat blades or pyramids. Typically, the microneedles are perpendicular to the plane of the device. The width of the microneedles can be about 15 to 40 gauge to obtain optimum penetration of the skin.

As shown in FIG. 2, the microneedles are typically spaced apart uniformly in rows and columns to form an array for contacting the skin and penetrating the stratum corneum. The spacing between the microneedles can be varied depending on the substance being administered either on the surface of the skin or within the tissue of the skin. Typically, the microneedles are spaced a distance of about 0.05 mm to about 5 mm.

The device 10 in the embodiment of FIGS. 1–3 includes three chambers 34 for administering different substances to the skin. Each array of microneedles corresponding to each of the chambers 34 are spaced apart a distance to avoid mixing and interaction between the different substances being administered.

Referring to FIG. 3, the chambers 34 can be filled with a suitable substance from a suitable supply container through the coupling member 38. A syringe 52 having a suitable outlet is attached to the coupling member 38. The syringe 52 is a standard syringe as known in the art which includes a syringe barrel 56, a plunger and plunger rod assembly 58 and a coupling complementing the coupling member 38, which in the illustrated embodiment is a Luer lock collar 54. The Luer lock collar 54 can be integrally molded with the syringe barrel or can be a separate collar which is snapped onto the tip 60 of the syringe barrel. The syringe barrel can be made of any suitable material including, for example, glass or plastic. The Luer lock collar 54 is threaded onto the coupling member 38 to form a fluid-tight seal. The substance in the syringe is injected through the opening 36 into the chamber 34. A suitable check valve 61 or other closure can be included in the coupling member 38 to prevent the backflow of the substance from the chamber 34.

In further embodiments, the chamber 34 can include a dried or lyophilized pharmaceutical agent 62. The dried pharmaceutical agent 62 can be applied as a coating on the bottom, top or side wall of the chamber or placed loosely within the chamber. A suitable solvent or diluent such as distilled water or a saline solution is injected through the opening 36 into the chamber 34 shortly before or during use to solubilize and reconstitute the pharmaceutical agent. The solvent or diluent can be injected into the chamber 34 from a syringe or other container.

Figure 4:
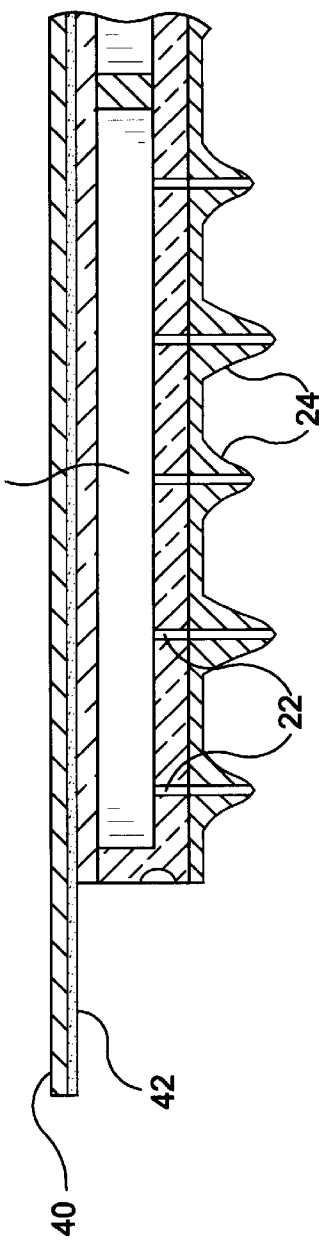
FIG. 4 is a partial side view of a transdermal delivery device according to a further embodiment of the invention, showing microneedles of different length.

Typically, the microneedles are uniformly spaced apart to form an array and have a substantially uniform length and width. In a further embodiment shown in FIG. 4, the microneedles have varying lengths to penetrate the skin at different depths. Varying the length of the microneedles allows the pharmaceutical agent to be delivered at different depths in the skin and can increase the effectiveness of the injection. A microneedle device with microneedles of different lengths is particularly effective in delivering a vaccine into the cells into or below the stratum corneum to increase the immunological efficiency of the vaccine by targeting an optimum absorption site. The microneedles can have lengths ranging from about 10 microns to about 40 microns. The microneedles are preferably arranged in the array with alternating lengths. Generally, the array includes microneedles having two different lengths. In other embodiments, the array can have microneedles of several lengths ranging from about 10 microns to about 40 microns. The effectiveness of the presentation of antigens to Langerhans cells is generally increased by providing the microneedles in varying lengths since the delivery of the vaccine to the optimum site is increased.

A substance is delivered to a patient using the device of FIGS. 1–4 by placing the microneedles against the skin and pressing or rubbing to enable the microneedles to penetrate the stratum corneum. The cover sheet 40 is attached to the skin by the adhesive. A syringe 52 or other dispensing container is coupled to the device 12 and the substance is introduced into the chambers 34 and through the microneedles 24. A suitable dispensing container can be, for example, a dispenser sold by Becton Dickinson and Company under the tradename Uniject. The syringe 52 is able to apply sufficient force to deliver the substance directly into the skin below the stratum corneum without the microneedles penetrating the dermis. The force is applied to provide a rapid delivery of the substance into the intradermal layer below the stratum corneum so that the device 12 can be removed from the skin after a short period of time. It typically is unnecessary to have the device remain attached to the skin for extended periods of time as in conventional sustained release devices. Alternatively, the device can remain attached to sufficient time to allow the substance to be absorbed into the skin.

In further embodiments, the syringe is used to fill the chambers with a pharmaceutical agent or diluent and is then removed from the device. Then the device is pressed against the skin so that the microneedles penetrate the stratum corneum. The pressure applied to the device enables the substance to be delivered below the stratum corneum. In still further embodiments, the device is rubbed against the skin to abrade the stratum corneum to enhance the delivery of the substance.

Figure 5:
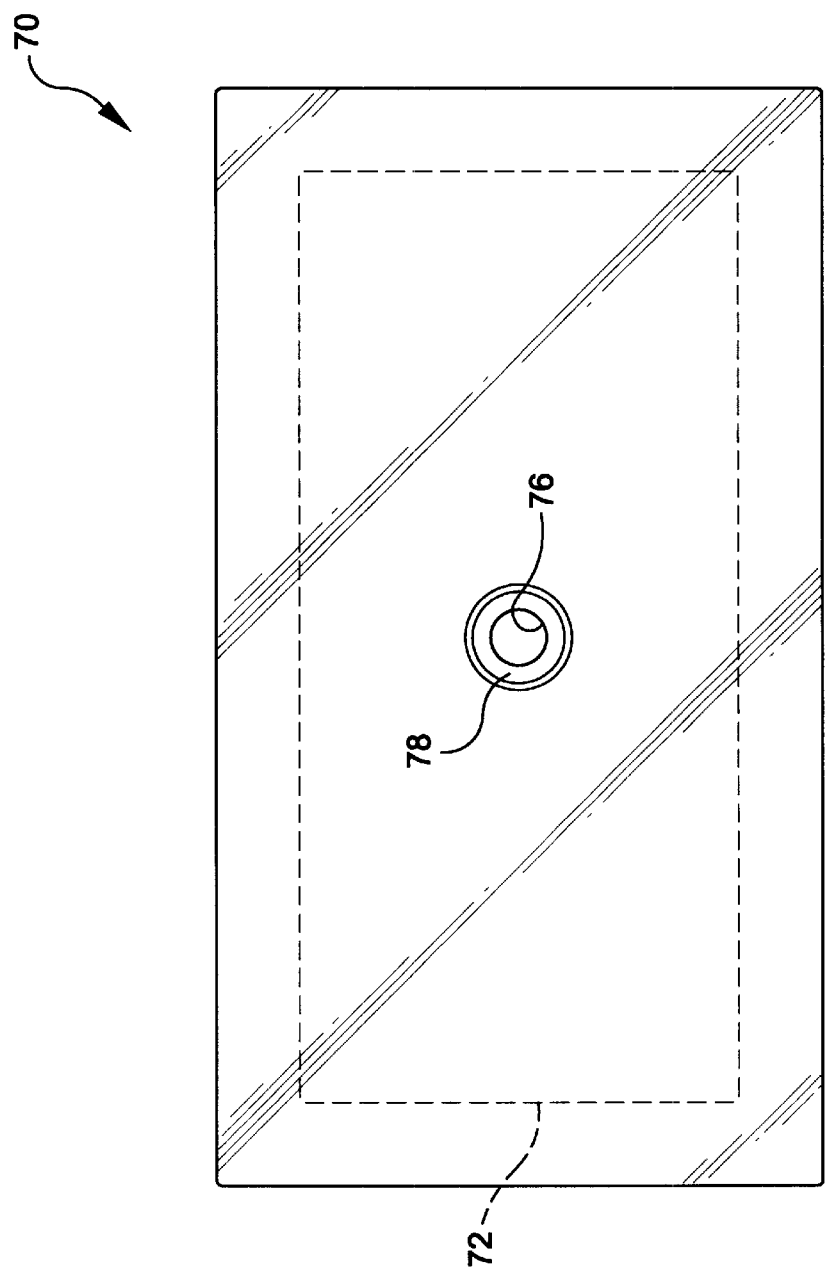
FIG. 5 is top view of the transdermal delivery device of FIG. 4.
Figure 6:
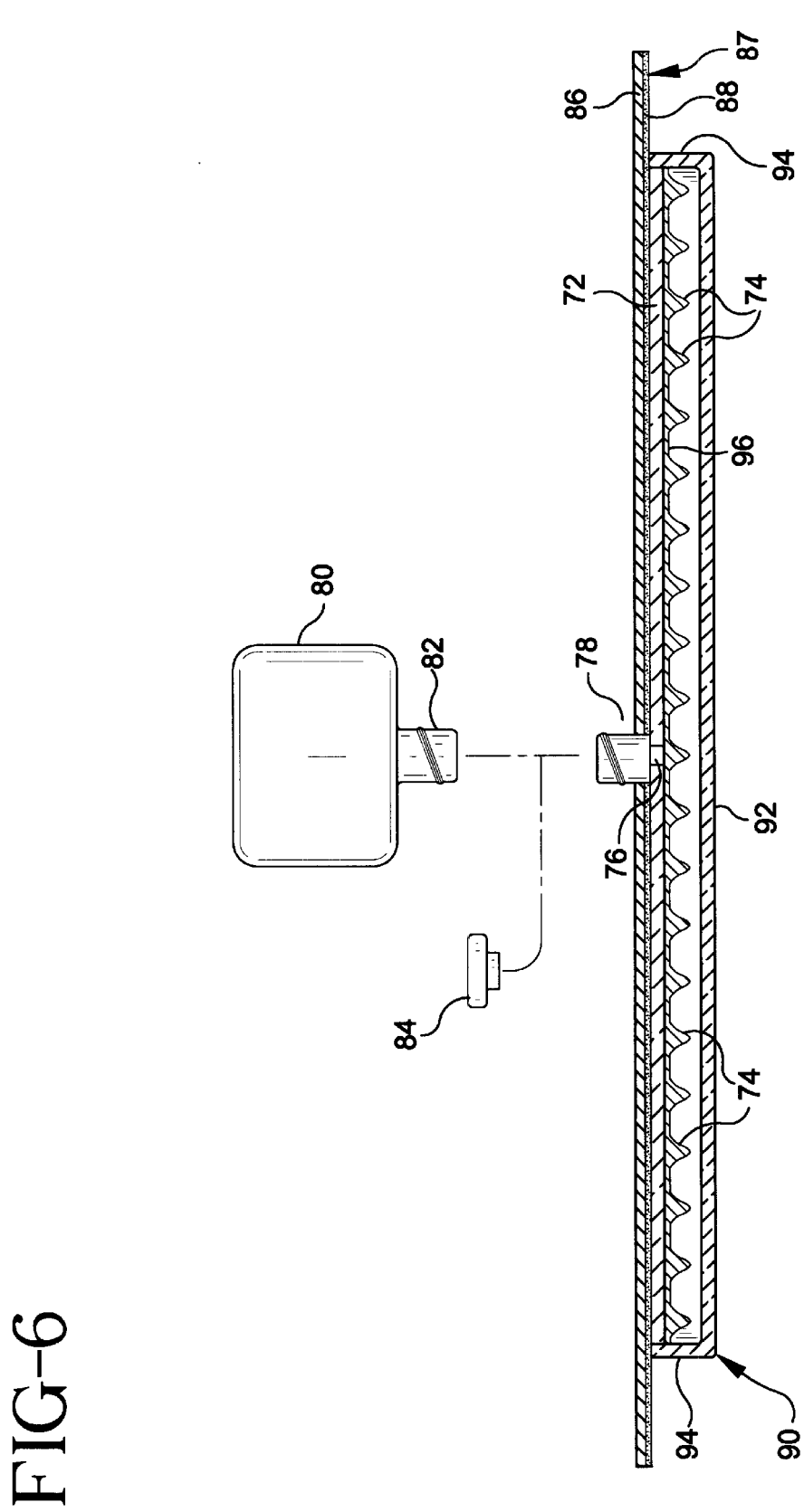
FIG. 6 is side elevational view in partial cross-section showing a supply container for supplying the device of FIG. 4 with a pharmaceutical agent.

A further embodiment of the intradermal delivery device is illustrated in FIGS. 5–7. Referring to FIGS. 5 and 6, the transdermal delivery device 70 includes a substantially flat base 72 having an array of microneedles 74 for the delivery of the substance being administered. Unlike the embodiment of FIG. 1, the microneedles 74 are substantially solid with no openings or passages through the microneedles. A central inlet port 76 is positioned in substantially the center of the base 72. A coupling member 78, such as a Luer lock collar, is attached to the base 72 over the inlet port 76 for supplying a substance to the microneedle 74. A suitable container having an internally threaded Luer lock collar 82 is provided for coupling with the collar 78 and introducing a substance through the inlet port 76 to the microneedle 74. The container 80 is illustrated as a flexible plastic container which can be compressed to force the substance from the container through the inlet port 76. Alternatively, a syringe having a Luer lock collar can be used for introducing the substance through the inlet port 76. An optional closure cap 84 can be removably attached to the Luer lock 78 to temporarily close the inlet port 76. The cap 84 can be an externally threaded cap for engaging the threads on the Luer lock 78 or can be a stopper-like member for fitting into the passageway of the Luer lock 78.

A flexible sheet material 86 having an adhesive layer 88 is applied over the upper surface of the base 72 and is attached to the base by the adhesive 88. As shown in FIGS. 5 and 6, the sheet 86 is larger than the dimension of the base 72 and overlaps on each of the sides to provide an exposed area 87 of adhesive for attaching the device to the skin of a patient. A removable cover 90 encloses the microneedles 74 to protect the microneedles from damage prior to use. In the embodiment illustrated, the cover 90 has an outer wall 92 and side walls 94 extending substantially perpendicular to the outer wall 92. The upper ends of the side wall 94 attach to the adhesive layer 88 of the sheet 86 to enclose the microneedles 74. The cover 90 can be separated from the adhesive 88 prior to use to expose the microneedles 74.

Referring to FIG. 7, the bottom surface 96 of the base 72 is provided with a plurality of channels 98 formed in the bottom surface. The channels 98 extend between the microneedles 74 from the inlet port 76 outwardly toward the edges of the base 72. In the embodiment illustrated, eight channels are illustrated extending substantially radially outward from the inlet port 76. In further embodiments, additional channels can be included branching outward from the channels 98 to direct the substance being administered to the microneedles 74. The channels 98 are illustrated as being straight, although in further embodiments, the channels can be curved and branched depending on the dimension of the base 72, the distribution of the microneedles 74, and the desired distribution of the substance being administered.

The channels 98 extend between the microneedles 74 to supply the microneedles with the substance being administered. In use, the base 72 is applied to the skin of the patient being treated so that the microneedles 74 penetrate the stratum corneum. The base 72 can be pressed against the skin to cause the microneedles to penetrate the stratum corneum and define a delivery site into the intradermal tissue. The adhesive 88 of the sheet 86 is pressed against the skin to secure the base to the skin over the delivery site and form a seal around the perimeter of the base 72.

In further embodiments of the invention, the base may be moved or rubbed during attachment to the skin to abrade the outermost portion of the stratum corneum of the skin and thereby enhance the penetration of the microneedles through the stratum corneum and the delivery of the pharmaceutical agent to the epidermis. Abrading the skin to remove a portion of the stratum corneum enhances absorption of a vaccine to promote an immune response. After the base is attached to the skin, the substance is supplied through the port 76 from a syringe or other container to feed the substance along the channels 98 and to the microneedles 74. The force supplied by the syringe or other container used for introducing the substance through the inlet port 76 directs the substance to the areas in the vicinity of the microneedles 74. The channels 98 direct the substance to the abraded area of the stratum corneum to deliver the substance to the skin for absorption by the body.

Generally, the substance being administered is a solution or dispersion of a pharmaceutical agent which is injected through the inlet port 76. Alternatively, the substance can be a fluid colloid in the form of a sol or a gel. Vaccines can be delivered in any liquid form as known in the art. In a further embodiment of the invention, the channels 98 are filled with a lyophilized or dried pharmaceutical agent. A suitable solvent or reconstituting liquid is injected through the inlet port 76 and directed along the channels 98 to dissolve and reconstitute the pharmaceutical agent. The reconstituted pharmaceutical agent is then directed to the microneedles for delivering through the stratum corneum to the epidermis.

Figure 8:
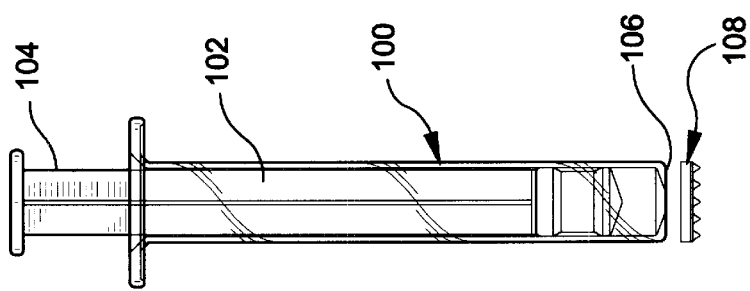
FIG. 8 is a side view of a further embodiment of the invention, in which a syringe barrel is provided with a microneedle tip.

In a further embodiment of the invention, illustrated in FIG. 8, a syringe 100 having a syringe barrel 102 is provided with a microneedle tip 106. A plunger rod 104 is provided to dispense the contents of the syringe. The tip 106 includes a plurality of microneedles 108 having a length sufficient to penetrate the stratum corneum. In the embodiment illustrated, the needles 108 have central passages extending through the lengths of the needles for communicating with the syringe barrel 102 and directing the substance through the stratum corneum of the patient.

Figure 9:
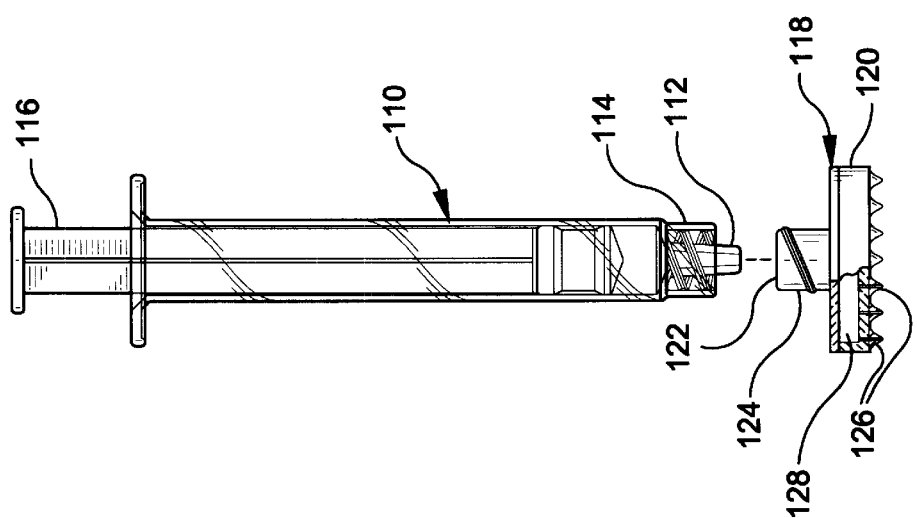
FIG. 9 is a partial cross-sectional side view of a further embodiment of the invention, in which a syringe with a Luer lock collar is coupled to a delivery device having a plurality of microneedles.

Referring to FIG. 9, a further embodiment of the invention uses a syringe 110 having a tip 112 with a Luer lock collar 114, a plunger rod assembly 116 that slides within a syringe barrel 118 to dispense the contents. A microneedle tip 118 includes a housing 120 having an inlet port with a Luer lock collar 124 in a manner similar to the embodiment of FIG. 1. A plurality of microneedles 126 are attached to the bottom surface of the housing 120. The microneedles 126 include a channel extending through the microneedles and through the bottom surface of the housing. The microneedles 126 are substantially the same as in the embodiment of FIG. 1. The housing 120 defines a reservoir 128 for directing the substance through the microneedles 126. In use, the syringe 110 is coupled to the Luer lock collar 124 and the microneedles 126 are pressed against the skin of the patient to penetrate the stratum corneum. The plunger rod assembly 116 is then depressed to express the substance from the syringe through the housing 120 and through the microneedles to deliver the substance to the skin.

The delivery device of the invention is generally designed to be a disposable, single-use device. The device can be used safely and effectively for intradermal, especially intraepidermal, delivery of a pharmaceutical agent or other substance. The device is particularly suitable for introducing a vaccine intradermally, especially intraepidermally, for efficiently delivering a small amount of the vaccine antigen for presentation to the Langerhans cells. The Langerhans cells are a type of intradermally located dentritic cell which take up and transport foreign material to draining lymph nodes for further amplification of immune response. The length, width and spacing of the microneedles can varying depending on the pharmaceutical agent being administered or required to penetrate or pierce the stratum corneum to the optimum depth for the specific pharmaceutical agent being administered. When delivering a vaccine, the microneedles are dimensioned to target the optimum intradermal, especially intraepidermal, delivery site to promote the desired immune response.

In certain embodiments illustrated, the delivery devices include inlet ports for injecting a pharmaceutical agent into a reservoir and through the microneedles. In other embodiments, the device can be prefilled with a pharmaceutical and the tips of the microneedles can be closed with a suitable closure, such as, for example, an adhesive sheet that can be peeled from the microneedles prior to use.

Alternatively, a cover having a soft pliable member can be attached to the bottom surface of the device such that the pliable member contacts the microneedles to seal the openings. The cover can then be removed from the device prior to use.

The delivery devices of the present invention are generally clean and sterile and packaged in suitable sterile pouches. In the process of administering a substance, the device is removed from the sterile pouch, the cover is removed from the device, and the device is placed on the skin and secured in place by the adhesive on the outer patch. The device can be rubbed slightly to abrade the skin's stratum corneum layer to allow the microneedles to penetrate the skin and increase the exposure of the layers of skin below the stratum corneum for more direct communication with the underlying tissue. The device is pressed down so that the microneedles penetrate the skin to the desired depth. A syringe is attached to feed the substance into the reservoir and into the desired intradermal layer of the skin. When the device contains a dried pharmaceutical agent in the reservoir, a diluent is introduced to the reservoir to solubilize or reconstitute the pharmaceutical agent. The device remains in contact with the skin for a sufficient period of time to deliver an effective amount of the substance to the patient. Thereafter, the device is removed from the skin and the area of the skin is covered with a suitable protective bandage.

The intradermal delivery device of the present invention provides a reliable way to deliver individual and multiple pharmaceutical agents in small doses by an intradermal route. The microneedles of the delivery device limit the penetration of the needles to prevent inadvertent deep penetration into the tissue as in conventional needles. The microneedles are also less painful to the patient and exhibit a lower incidence of skin necrosis common with some DNA vaccines. The multiple chambers of the delivery device enable the administration of multiple vaccines, adjuvants and pharmaceutical agents simultaneously without prior reformulation or combination of the pharmaceutical agents. Administering the pharmaceutical agents through the skin provides efficient presentation of antigen, vaccine or adjuvant, thereby reducing the dose of the vaccine delivery. The delivery device is particularly suitable for DNA vaccines which may be a stable dry protein product. Currently, the only delivery route is a standard needle and syringe, or specialized equipment referred to as gene guns which require formulation of the antigen so as to remain attached to gold beads. In the illustrated device, a small amount of a diluent supplied to the delivery device propels the vaccine particles through the hollow microneedles or through channels to solid microneedles and into intradermal tissue.

While several embodiments have been shown to illustrate the present invention, it will be understood by those skilled in the art that various changes and modifications can be made therein without departing from the scope of the invention as defined in the appended claims.

What is claimed is:

1. A delivery device for introducing a substance into or below the stratum corneum of a patient, said device comprising:
    a top wall having a top surface, a bottom surface, and at least one opening extending between said top and bottom surfaces;
    a bottom wall having an inner surface and an outer surface coupled to said top wall by at least one side wall and spaced from said top wall to define a reservoir therebetween for containing said substance, said bottom wall having a plurality of openings extending between said inner and outer surfaces, and said reservoir being in fluid communication with at least one of said at least one opening in said top wall;
    a coupling member attached to said top wall for supplying a fluid selected from the group consisting of said substance, a diluent, and a solvent for said substance through said at least one opening in said top wall and into said reservoir with sufficient pressure to expel said fluid through said plurality of said bottom wall openings at a predetermined rate; and
    a plurality of individual hollow microneedles attached to and in contact with said outer surface of said bottom wall and being in fluid communication with said openings in said bottom wall and having a length sufficient to penetrate or pierce the stratum corneum without penetrating into the dermis of said patient; and further comprising
        at least one internal wall extending between said top and bottom walls to divide said reservoir into at least two chambers, each of said chambers communicating with at least one opening in said top wall and with at least one opening in said bottom wall.

2. The device of claim 1, wherein said coupling member is a Luer lock collar.

3. The device of claim 2, further comprising a syringe removably coupled to said Luer lock collar for supplying a fluid to said reservoir and expelling the fluid through said opening in said bottom wall.

4. The device of claim 1, wherein each of said chambers includes a dry pharmaceutical agent.

5. The device of claim 4, wherein said top wall includes a coupling member attached to said top wall and surrounding said opening in said top wall.

6. The device of claim 1, further comprising a flexible film having a dimension greater than a dimension of said top wall, said film including an adhesive layer on a bottom side thereof, and being attached to said top wall by said adhesive layer and overlying said top wall and extending beyond said top wall a distance whereby said film is able to attach said device to the skin of a patient.

7. The device of claim 1, further comprising a cover removably coupled to said bottom wall and enclosing said microneedles.

8. The device of claim 7, wherein said cover includes an outer wall and at least one side wall, said side wall being frictionally attached to said delivery device.

9. The device of claim 1, wherein said reservoir contains a substantially dry pharmaceutical compound, which can be reconstituted by introducing a solvent into said reservoir.

10. The device of claim 1, wherein said microneedles are of different lengths.

11. The device of claim 1, wherein said microneedles include a tip for penetrating the stratum corneum of the skin and a fluid passage for directing a fluid from said reservoir to said tip.

12. An intraepidermal delivery device according to claim 1, wherein the length of the plurality of hollow microneedles is about 5 to 200 microns.

13. An intraepidermal delivery device according to claim 1, wherein each of the individual hollow microneedles has a width from about 15 to about 40 gauge.

* * * * *